United States Patent [19]
Rogers

[11] Patent Number: 5,068,504
[45] Date of Patent: Nov. 26, 1991

[54] SEAT CUSHIONS AND BODY SUPPORTS, AND FITTING INSTRUMENTS FOR THE SAME

[76] Inventor: John E. Rogers, P.O. Box 1437, Blue Jay, Calif. 92317

[21] Appl. No.: 486,690

[22] Filed: Mar. 1, 1990

Related U.S. Application Data

[63] Continuation of Ser. No. 323,672, Mar. 15, 1989, abandoned.

[51] Int. Cl.$^5$ .............................................. H01H 3/02
[52] U.S. Cl. .............................. 200/85 R; 200/86 R; 200/302.1; 340/666
[58] Field of Search .................. 340/666, 667, 573; 200/275, 505, 508, 512, 85 R, 85 A, 86 R, 86 A, 302.1

[56] References Cited
U.S. PATENT DOCUMENTS

| | | | |
|---|---|---|---|
| 3,718,791 | 2/1973 | Szablowski | 200/86 R |
| 4,401,896 | 8/1983 | Fowler | 200/86 R |
| 4,551,713 | 11/1985 | Aossey | 200/85 R |
| 4,565,910 | 1/1986 | Musick | 200/85 R |
| 4,617,433 | 10/1986 | Hoshikawa | 340/666 |
| 4,845,323 | 7/1989 | Beggs | 200/85 R |

*Primary Examiner*—Gerald P. Tolin
*Attorney, Agent, or Firm*—Natan Epstein

[57] ABSTRACT

A peak pressure sensor, for insertion between a body support pad or the like and an anatomical portion supported thereon, has a envelope, pliable electrically conductive sheets on opposite inner surfaces of the envelope, conductors for connecting each sheet to an alarm circuit, and a fluid pressurizing the envelope to a predetermined internal pressure so as to normally hold apart the conductive sheets. The sheets are movable into electrical contact by sufficient pressure applied locally to any relatively small portion of a sensing area on the exterior of the envelope, thereby to detect a peak pressure on the anatomical portion in excess of the internal envelope pressure.

4 Claims, 1 Drawing Sheet

SEAT CUSHIONS AND BODY SUPPORTS, AND FITTING INSTRUMENTS FOR THE SAME

This application is a continuation of Ser. No. 323,672 filed Mar. 15, 1989 and now abandoned.

BACKGROUND OF THE INVENTION

1. Field of the Invention

The present invention pertains generally to the field of body supporting and cushioning devices and more particularly relates to seat cushions and body supports directed to meet the needs of persons who are chair-bound for medical or other reasons over protracted periods of time, and diagnostic devices for properly fitting such cushions to the needs of particular individuals.

2. State of the Prior Art

Much inventive activity has been directed to the development of various cushioning and support devices for use by the handicapped, the chair-bound, the bed-ridden, and generally by non-ambulatory individuals. A recurrent problem encountered by such persons is the increased likelihood of ulceration and damage to skin and underlying tissues at areas of the body which are subjected to continuous moderate or high levels of pressure over periods of hours and sometimes days without relief. Such conditions lead to the formation of decubitus ulcers, commonly known as bed sores.

Protracted pressure against any portion of the skin has the effect of diminishing- or cutting off peripheral vascular flow to that area. If impairment of blood flow to the affected area is sufficiently prolonged, the tissues underlying the affected skin area will be starved of nutrients and suffer progressive damage. Typically it is the underlying soft tissues which are first damaged, until eventually the skin undergoes necrosis and ulcerates in progressive manner, and unless the pressure on the area is removed, such ulcers can become deep open wounds which are difficult to treat and slow to heal.

Even moderate levels of pressure over relatively brief periods of time can lead to significant skin and tissue damage and much effort has therefore been expended towards providing improved seat cushions and back-pads for non-ambulatory persons confined to wheel chairs. The difficulties encountered by such persons are frequently compounded by medical conditions which may insensitize the person to progressive skin and tissue damage until such damage has reached advanced and serious stages, and by conditions which deprive the individual of any ability to reposition him or herself so as to relieve continuous pressure on any particular portion of the anatomy to thus stem the formation of ulcerations or other soft tissue damage by periodically shifting position.

One anatomical area which is particularly susceptible to soft tissue damage in persons confined to a sitting position over protracted periods of time is the skin and soft tissue overlying and adjacent to the ischial tuberosities of the pelvis, and the sacral and coccyx areas, particularly in the case of those with spinal cord injury. In such cases, utmost care must be taken to minimize pressure levels on certain portions of the anatomy which are particularly susceptible to the formation of decubitus ulcers, and to distribute the pressures exerted by cushions or other body support devices in a manner which reduces peak pressure levels to acceptable levels considered to be relatively benign over longer periods of time.

There is a continuing need for more effective, simpler and easier to fit devices in furtherance of the above mentioned objectives.

SUMMARY OF THE INVENTION

An improved peak-pressure sensor for diagnostic use with body support devices comprises an inflatable envelope of pliable material, substantially pliable electrically conductive contact sheets affixed to opposing inner surfaces of the envelope in mutually facing relationship, conductors for electrically connecting the sheets to an alarm circuit; a fluid permanently sealed at a predetermined internal pressure to normally hold apart the contact sheets, the conductive sheets being movable into mutual electric contact by sufficient inward pressure applied locally to a sensing area on the exterior of the envelope. The envelope may consist of two pliable impermeable sheets sealed together along common edges. The conductive contact sheets are thin metallic sheets in which portions are slit into narrow strips or ribbons, preferably within a central area of each sheet, thin strips being held together by a common continuous periphery of the sheet, so that the sheets are made more readily compliant for movement with the envelope wall, to provide relatively large and substantially continuous electrical contact areas, and are responsive to local pressure applied within a small to the region of the sensing area for detecting excessive peak pressure levels by actuating an alarm circuit connected contact sheets.

The minimum external pressure required to actuate such a sensor is determined primarily by the internal pressure of the pre-charged envelope. Two or more such sensors, each pre-charged to a different pressure, may be stacked for ascertaining, to an approximation, the pressure to which is subjected a given anatomical portion by a cushion or other body support device

DETAILED DESCRIPTION OF THE PREFERRED EMBODIMENTS

Figure 1:
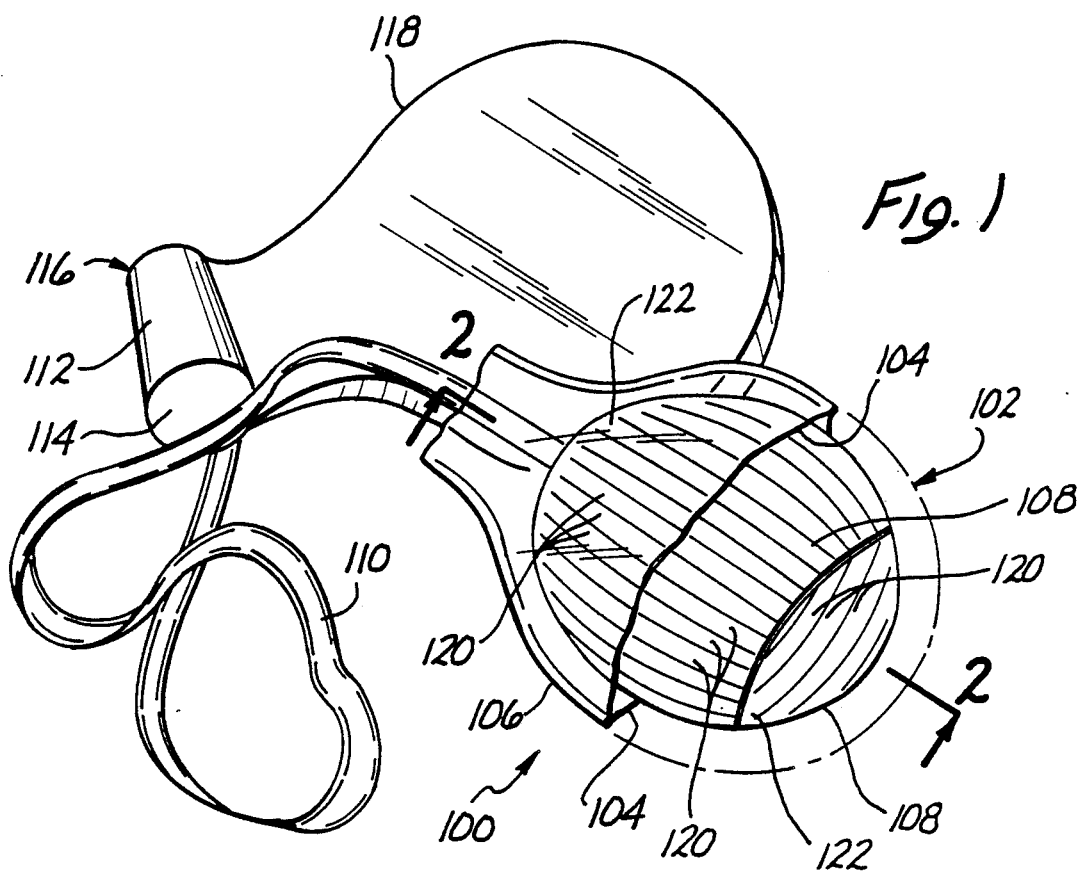
FIG. 1 is a perspective view partly broken away of a pre-charged p peak-pressure sensor unit for use with body support devices and cushions.
Figure 2:
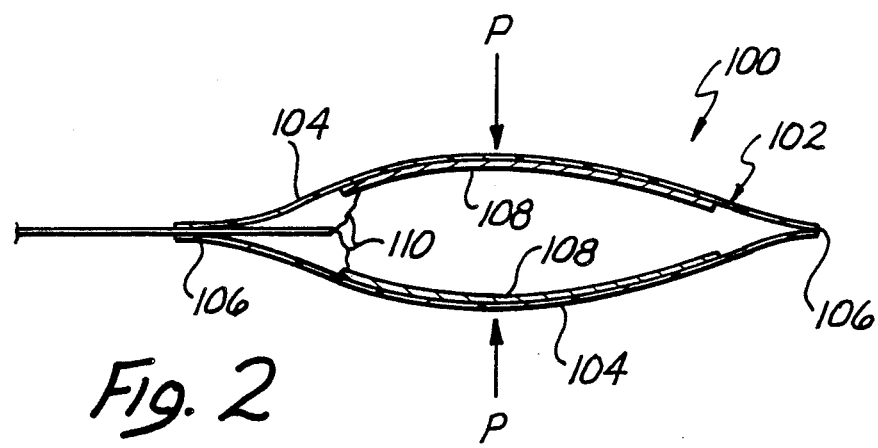
FIG. 2 is a cross-section of the pneumatic switch element taken along 2—2 in FIG. 1.
Figure 3:
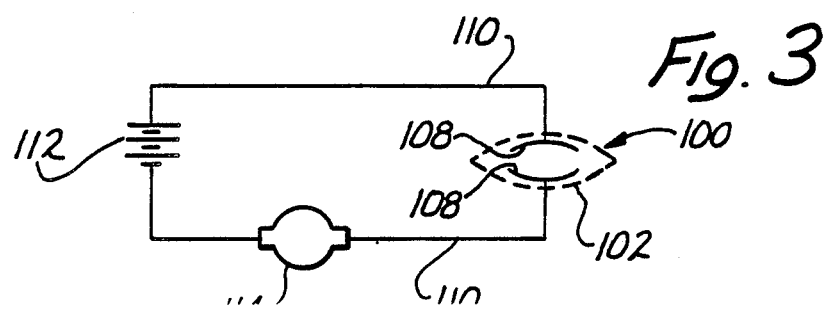
FIG. 3 is an electrical schematic of the pre-charged pneumatic peak pressure sensor of FIG. 1.

FIGS. 1, 2 and 3 illustrate an improved seat cushion 10 particularly useful for use by chair-bound individuals such as those having spinal cord injury. The cushion 10 includes a slab 12 of a resilient, compressible material such as a foamed synthetic material. The slab 12 is preferably rectangular with an upper supporting or seat surface 14, an undersurface 16, a forward edge 18, a rear edge 20 and two side edges 22. The slab 12 has in its upper surface 14, intermediate the two sides 12, an ischial recess or cavity 24 which is open at the rear edge 20 as illustrated, and which extends from the rear edge 24 forwardly towards the forward edge 18 approximately one third ($\frac{1}{3}$) of the length of the pad, at least four inches for children and seven inches for adults, as best seen in FIG. 3.

Turning to FIGS. 1-3, yet another aspect of the present invention relates to improvements in diagnostic devices for use in fitting cushions, pads or other body support devices to the needs of particular individuals. FIGS. 1 and 2 show a pneumatic peak pressure sensor 100 which includes an outer envelope 102 made up of two air impermeable sheets 104 joined along a common edge 106. For example, two generally circular sheets of thin vinyl may be heat sealed along their periphery 106 to make up an air tight envelope 102. Two thin metallic contact sheets 108 are adhesively affixed to opposite inner surfaces of the envelope 102, as shown in FIG. 14, one contact sheet 108 to the opposing inner surfaces of each envelope sheet 104. A pair of electrical conductors 110 are connected, one to each contact sheet 108 within the envelope 102 and led through an air tight passage to the exterior of envelope 102. The interior of the pneumatic envelope 102 is then pressurized, as by compressed air, to a predetermined pressure level which can be determined empirically as being sufficient to maintain the contact sheets 108 in normally spaced apart relationship, as shown in FIG. 2 against a pressure P acting on the exterior of the envelope 102 tending to bring the contact plates 108 together. This pressure P is then the peak pressure which it is considered unacceptable to exceed against any portion of a particular cushion user's anatomy. When such pressure is exceeded against the exterior of the envelope 102, some portions of the plates 108 are brought into electrical contact, which condition can be used to actuate a suitable alarm in a simple circuit such as depicted in FIG. 15 comprising the pneumatic switch 100 contacted in series to a battery 112 and audible alarm or buzzer 114. The entire alarm circuit may be assembled in a compact arrangement shown in FIG. 1 where both battery 112 and buzzer 114 are housed in a small housing 116 which is physically attached to a case 118 in which the envelope 100 is normally stored when not use, and conductors 110 suitably insulated and physically protected interconnect the housing 116 to the sensor 100.

One novel feature in the peak pressure sensor 100 is the pre-charging of the envelope 102 to a sufficient internal pressure, e.g. 10 mm air pressure above sea level atmospheric, so as to detect contact of the plates 108 as indicative of a given external pressure on the envelope 102. This pre-charging is a permanent internal pressurization of the envelope so as to provide a convenient lightweight and ready to use pneumatic sensor which can be easily inserted as necessary between the user's anatomy and the cushion or other support device, for detecting excessive pressure levels and to allow proper fitting of the cushion to the user's needs.

A further improvement in the peak pressure detector 100 is the use of metallic contact sheets 108, made preferably of thin copper sheet, e.g. about 3 mil thick adhesive backed copper sheet, and which are slit into relatively thin ribbons or strips 120, desirably no more than ¼ inch wide and preferably about ⅛th inch wide, over a large central portion of each sheet 108. The ends of the strips 120 are interconnected by a common uncut periphery 122 of each sheet 108. As shown in FIG. 1, the opposing conductive sheets 108 are slit in mutually transverse directions, such that the strips 120 on one sheet 108 lie across but normally spaced from the strip 120 on the opposite sheet 108. The resultant contact sheets 108 are highly pliable and flexible for flexing movement together with the envelope walls 104, which may be of 10 mil thick vinyl sheet, in response to pressure differences across these walls. Furthermore, the increased pliability of the electrical contact sheets 108 allows detection of locally applied pressures, i.e. pressures applied to a small portion of the exterior surface of the envelope sheets 104 which pressure is sufficient to locally indent the envelope wall 104 and is not distributed over the entire surface of the wall 104. As a result, the highly pliable contact sheets used with relatively large e.g. two inches or more in diameter envelopes 102 produce a sensitive peak pressure detector as opposed to an average pressure detector Still further, the slit sheets 108 provide for virtually continuous electrical contact at any point along the surface as opposed to previously used wire grids or discrete contact points spaced apart in comparable switches, which can provide inferior resolution and less reliable contacts. The pneumatic switch or sensor 100 can be made in two sizes found useful, one a smaller envelope measuring about 1 inch by ⅞ths inch, and a larger size measuring about 4 by 2 inches in envelope size, the copper sheets being slightly smaller in both cases to avoid false contact at the envelope edges. The smaller sensor is useful at anatomical locations where the pressure point of concern can be visualized and is readily accessible, as under a heel. The larger sensor size is preferable for use under larger, heavier portions such as the buttocks or seat areas where the bony protuberances are not readily visualized and access is difficult as under a sitting or reclining individual.

It may be convenient in some cases to stack two or more sensors 100, each pre-charged to a different internal pressure so as to determine to a degree of approximation peak pressures falling within the pressure range represented by the stacked pressure sensors 100. A number of envelopes 102 may be affixed together adhesively or otherwise into a detector assembly for diagnostic use in a manner similar to the use of a single envelope detector 100. In a stacked arrangement, the envelope 102 of lowest internal pressure will make electrical contact first and so on up to the highest pressure envelope. Each envelope is connected to a corresponding signally device which are thus triggered sequentially from lowest pressure to highest pressure indication.

While particular embodiments of each aspect of the invention have been described and illustrated for purposes of example and clarity, it will be understood that many changes, substitutions and modifications to the same will become apparent to those possessed of ordinary skill in the art without departing from the spirit and scope of the invention as defined in the following claims.

What is claimed is:

1. An improved peak pressure sensor for use with body support devices, comprising:

an inflatable envelope comprised of two pliant impermeable sheets sealed along common edges;

substantially pliable electrically conductive sheets affixed to opposing inner surfaces of said envelope in mutually facing relationship;

conductor means for electrically connecting said conductive sheets to an alarm circuit;

a fluid permanently sealed in said envelope and pressurizing said envelope to a predetermined internal pressure so as to normally hold apart said conductive sheets;

wherein said conductive sheets are thin metallic sheets slit within a central area thereof into thin strips held together by a common continuous periphery of the sheet;

whereby said metallic sheet provides a relatively large and substantially continuous contact area compliant to three dimensional cupping and responsive to peak pressure levels acting on any arbitrarily small portion of said central area by actuating an electrical alarm circuit connected between said sheets;

characterized in that said metallic sheets are slit in mutually transverse directions so that electrical contact can be achieved at a intersection between any two strips on the opposite sheets when said impermeable sheets are pressed together to thereby respond to localized peak pressures on said central area rather than average pressure distributed over said central area.

2. The pressure sensor of claim 1 wherein said fluid is air contained at a pressure above sea level atmospheric.

3. The pressure sensor of claim 1 wherein said envelope is at least about two inches in diameter, said metallic sheets are slightly smaller than two inches, and said strips are no more than about ¼ inch in width.

4. The pressure sensor of claim 3 wherein said impermeable sheets are vinyl sheets and said metallic sheets are copper sheets adhesively bonded to said vinyl sheets.

* * * * *